(12) United States Patent
Patel Framroze

(10) Patent No.: US 8,945,523 B2
(45) Date of Patent: Feb. 3, 2015

(54) SKIN LIGHTENING COMPOSITION FOR HYPERPIGMENTED SKIN

(75) Inventor: Bomi Patel Framroze, Palo Alto, CA (US)

(73) Assignee: Bomi Patel Framroze, Toronto (CA)

( * ) Notice: Subject to any disclaimer, the term of this patent is extended or adjusted under 35 U.S.C. 154(b) by 1029 days.

(21) Appl. No.: 12/521,353

(22) PCT Filed: Dec. 26, 2006

(86) PCT No.: PCT/IB2006/055032
§ 371 (c)(1), (2), (4) Date: Sep. 30, 2010

(87) PCT Pub. No.: WO2008/078154
PCT Pub. Date: Jul. 3, 2008

(65) Prior Publication Data
US 2012/0141397 A1    Jun. 7, 2012

(51) Int. Cl.
*A61K 8/00* (2006.01)
*A61K 8/18* (2006.01)
*A61Q 5/08* (2006.01)
*A61Q 19/02* (2006.01)
*A61K 8/02* (2006.01)
*A61K 8/73* (2006.01)
*A61K 8/60* (2006.01)

(52) U.S. Cl.
CPC ............... *A61K 8/735* (2013.01); *A61K 8/602* (2013.01); *A61Q 19/02* (2013.01)
USPC ........................................... 424/62; 424/401

(58) Field of Classification Search
None
See application file for complete search history.

(56) References Cited

U.S. PATENT DOCUMENTS

| 5,993,835 A * | 11/1999 | Mishima ................. 424/401 |
| 6,068,834 A | 5/2000 | Kvalnes et al. |
| 6,153,177 A | 11/2000 | Bartolone et al. |
| 2005/0147570 A1 * | 7/2005 | Nordsiek et al. ............. 424/59 |
| 2006/0183709 A1 * | 8/2006 | Alkayali .................... 514/54 |

FOREIGN PATENT DOCUMENTS

KR     2005026648 A  *  3/2005

OTHER PUBLICATIONS

Cosmetics Info, (website, 2013, Boric Acid).*
Gianeti et al (Dermatological Therapy, 2013, vol. 26, pp. 267-271, abstract provided).*
International Search Report of PCT/IB2006/055032, Mailing Date of Dec. 18, 2007.
R.K. Heaney et al., "The isolation and characterization of hyaluronic acid in egg shell", Biochimica et Biophysica Acta, vol. 451, pp. 133-142 (1976).

* cited by examiner

*Primary Examiner* — Brian-Yong Kwon
*Assistant Examiner* — Mark V Stevens
(74) *Attorney, Agent, or Firm* — Westerman, Hattori, Daniels & Adrian, LLP

(57) ABSTRACT

An improved skin composition intended for topical application to skin for lightening hyperpigmented skin is provided. The subject composition is characterized by incorporation of at least one carbohydrate-based melanin inhibiting agent selected from bearberry extract, ascorbyl glucoside, rutin and arbutin into an ultra low molecular weight aminoglycan polymer gel. It has been found that the skin composition of the present invention possesses improved skin penetration and significantly enhances the depigmenting effect of the active agents.

7 Claims, 1 Drawing Sheet

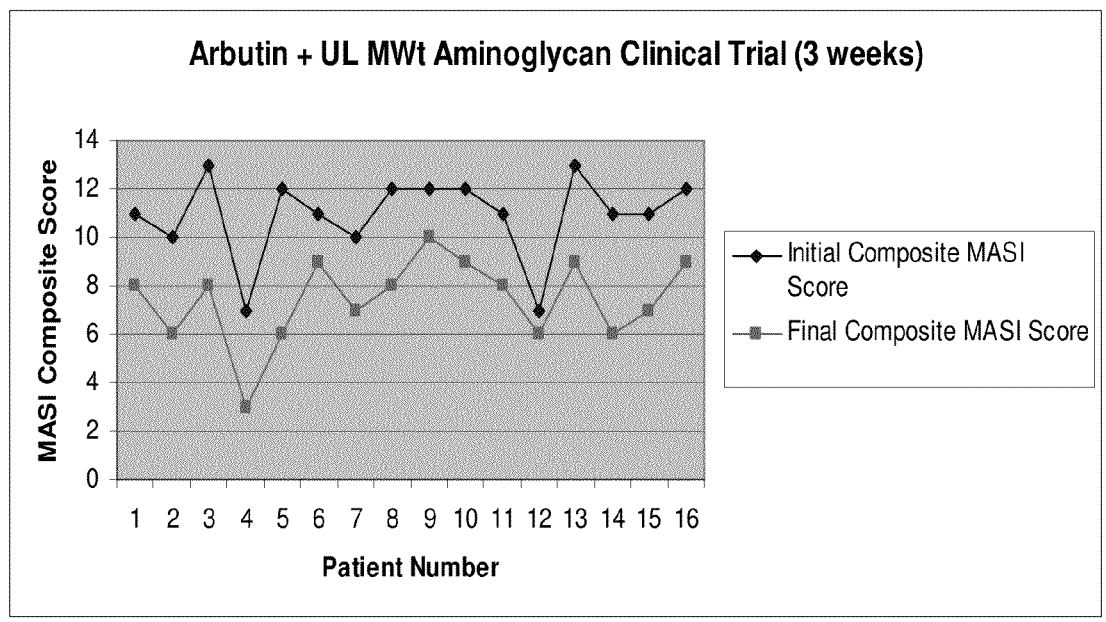

SKIN LIGHTENING COMPOSITION FOR HYPERPIGMENTED SKIN

FIELD OF THE INVENTION

This invention relates to a skin composition intended for topical application to skin for lightening hyperpigmented skin. More specifically, this invention relates to a skin composition that comprises at least one carbohydrate-based melanin inhibiting agent incorporated into an ultra low molecular weight aminoglycan polymer gel. This invention also relates to a method for lightening hyperpigmented skin, which comprises topically applying to the skin, an effective amount of the skin composition.

BACKGROUND OF THE INVENTION

Skin lightening cosmetics are used by millions of individuals for lightening their natural skin color for cosmetic reasons and the number of such users is on the rise. However, the use of skin lightening cosmetics varies considerably among cultures. A major cosmetic concern among Indian and other Asian populations is the appearance of dark circles (melasma) around the eye region. This occurs due to a site-specific increased melanin production called hyperpigmentation. Melanin is the pigment or coloring agent of skin and is produced in melanocytes which are the pigment forming cells found in the basal layers of the epidermis. Many cosmetic products have been reported to control the amount of melanin production in hyperpigmented skin. The majority of these products act by inhibiting the tyrosinase enzyme, which is the only essential enzyme needed in the production of melanin. A number of tyrosinase inhibitors are used in cosmetic compositions. Hydroquinone is one of the first tyrosinase inhibitors used in skin lightening. However, the prolonged topical use of this compound has been associated with a variety of disorders, including infectious dermatosis, contact eczema, extended dermatophytosis, ochronosis, periorbitary dyschromia, and necrotizing cellulites (Raynaud E. et al., Ann Dermatol Venereol 128(6-7):720-724, 2001). Hydroquinone has also shown genotoxic and mutagenic activities (Jagetia G. C. et al, Toxicol Lett 121(1): 15-20, 2001). Reports of toxicity have led to banning of hydroquinone in Europe for use as a depigmenting agent and in the United States also its use is limited to solutions of 2% or lower concentration (Journal of the European Academy of Dermatology and Venereology; Volume 20 Page 777—August 2006; Skin Therapy Letter Volume 9 Number 6, June-July 2004). Hydroquinone has also been used in combination with other compounds such as Kojic acid (U.S. Pat. No. 5,279,834). However, it has been reported that such compositions provide only temporary effect and hyperpigmentation returns if use of the composition is discontinued.

Compositions containing other tyrosinase inhibitors namely bearberry, arbutin, rutin and ascorbic acid either alone or in combination with other pharmaceutically acceptable agents have been reported in the art (U.S. Pat. No. 4,818,768, U.S. Pat. No. 5,980,904, U.S. Pat. No. 5,747,006, U.S. Pat. No. 6,123,959, U.S. Pat. No. 5,882,658, U.S. Pat. No. 6,077,503 and U.S. Pat. No. 6,641,845; Japanese Published Patent Applications: JP 10-279421, JP 10-279422; PCT Published Patent Applications WO 02/055047 and WO 06/090939).

Cosmetic compositions such as those described above seem to have a moderate improved effect in lightening or whitening the skin. However, many of the compositions are either only marginally effective or provide only temporary lightening effect. Accordingly, there still exists a need to develop an improved skin composition for topical application, having the desired degree of effectivity, when applied to affected areas of skin. The present invention fulfills this need and provides further related advantages.

SUMMARY OF THE INVENTION

The present invention provides a skin composition for lightening hyperpigmented skin, suitable for external use through topical application. The skin composition according to the present invention comprises at least one carbohydrate-based melanin inhibiting agent and an ultra low molecular weight aminoglycan polymer gel.

The skin composition according to the present invention possesses improved efficacy resulting from the incorporation of at least one carbohydrate-based melanin inhibiting agent selected from arbutin, bearberry extract, rutin and ascorbyl glucoside; into an ultra low molecular weight aminoglycan polymer gel.

The skin composition according to the present invention may optionally contain an antioxidant selected from vitamin E, vitamin A, tree tea oil, green tea extract, butylated hydroxyl anisole (BHA), butylated hydroxyl toluene (BHT) and ferulic acid or derivatives thereof, and the like.

The skin composition according to the present invention can further comprise a cosmetically acceptable ingredient suitable for use in such preparations, such ingredient may include emulsifiers, surfactants, emollients, essential oils, moisturizers, stabilizers viscosity modifiers, gelling agents, humectants, colorants and the like.

Furthermore, the skin composition according to the present invention can be in the form of a preparation that facilitates topical application, such as a cream, ointment, foam, lotion, plaster, and emulsion.

The present invention also includes a method for lightening hyperpigmented skin, which comprises topically applying to the skin an effective amount of the skin composition.

The skin composition according to the present invention can be used cosmetically to effect skin whitening. Accordingly, the present invention also includes the cosmetic use of the composition.

BRIEF DESCRIPTION OF THE DRAWINGS

FIG. 1 shows the results of clinical study involving use of the skin composition of the present invention in 16 subjects with mild to severe melasma typified by dark circles around the eyes.

DETAILED DESCRIPTION OF THE INVENTION

Before describing the present invention in detail, it is to be understood that the terminology used herein is for the purpose of describing particular embodiments only, and is not intended to be limiting.

It must be noted that, as used herein and in the appended claims, the singular forms "a," "an," and "the" include plural referents unless the context clearly indicates otherwise.

The term "at least" as used herein and in the appended claims, means that the skin composition of the present invention may contain one or more than one of the carbohydrate-based melanin inhibiting agents.

The terms "active agent," "topical agent" and "cosmetically active agent" are used interchangeably herein to refer to a compound that induces a desired physiological effect, and include agents that are therapeutically effective, prophylactically effective, or cosmetically effective.

The terms "hyperpigmented skin" and "hyperpigmentation" are used interchangeably herein to refer to a range of skin disorders caused by an increased production of melanin and results in localized areas of increase skin pigmentation. These disorders include, but are not limited to, melasma or melasma arising during pregnancy ("mask of pregnancy") or as a consequence of oestrone/progestogen contraception; other localized hyperpigmentations by benign melanocytic hyperactivity and proliferation, such as senile pigmental blemishes ("age spots"); disease-related hyperpigmentation; accidental hyperpigmentations such as those due to photosensitization, genetic makeup, chemical ingestion or other exposure, age, and post-lesional scarring.

The term "ultra low molecular weight aminoglycan" as used herein and in the appended claims refers to an aminoglycan with a molecular weight that is less than 100,000 Daltons, typically between 15,000 and 30,000 Daltons.

The term "cosmetically acceptable," as used herein means that a compound that is not biologically or otherwise undesirable, i.e., the compound may be incorporated into a topical formulation of the invention and administered to a subject without causing any undesirable biological effects or interacting in a deleterious manner with any of the other components of the formulation in which it is contained.

The terms "topical administration" and "topical application" are used interchangeably and in their conventional sense mean delivery of a topical agent or a cosmetically active agent to the skin.

The term an "effective amount" of a cosmetically active agent means a sufficient amount of the agent to provide the desired effect. The amount that is "effective" will vary from subject to subject, and it is not always possible to specify an exact "effective amount." However, an appropriate "effective amount" in any individual case may be determined by one of ordinary skill in the art using routine experimentation.

The term "enhanced efficacy," as used herein, means that the skin composition of the present invention exhibits an increased rate of visible lightening of the skin. Preferably, with continued use, the frequency of application required to achieve the desired level of lightening of the skin may decrease.

In accordance with the present invention, there is provided a skin composition for topical application to skin for lightening of the hyperpigmented skin.

Thus, the skin composition according to the present invention comprises a melanin inhibiting agent, particularly a carbohydrate-based melanin inhibiting agent incorporated in an ultra low molecular weight aminoglycan polymer gel.

The carbohydrate-based melanin inhibiting agent according to the present invention may be selected from arbutin, bearberry extract, ascorbyl glucoside, and rutin. The preferred carbohydrate-based melanin inhibiting agent is arbutin.

Arbutin is a naturally occurring hydroquinone-β-D-glucopyranoside. It is an active ingredient of the crude drug Uvae Ursi Folium traditionally used in Japan and also is contained in the leaves of pear trees and certain herbs. Arbutin is free from allergenic side effects that are reported for other tyrosinase inhibitors such as hydroquinone and kojic acid. Although arbutin is being used for whitening cosmetics, it is not easily absorbed into the skin because of its inability to penetrate the basal cells to physiologically desired concentrations.

Ascorbyl glucoside is a useful depigmenting agent. It is a new type of stable Vitamin C (ascorbic acid) that is not oxidized, but still shares the same physiological activation mechanism as ascorbic acid. Ascorbyl glucoside is commercially available.

Bearberry extract is an extract from the leaves of the bearberry plant *Arctostaphylos uva-ursi*. It is a natural, stable, highly-effective plant-based skin lightener that helps retard excessive melanin production without irritation.

Rutin is a flavonol glycoside. It is found in many plants, fruits and vegetables. However, the plant buckwheat ("*Fagopyrum esculentum maench*") is a major source of rutin. Rutin is well-known for its anti-oxidant property.

Use of all the aforementioned carbohydrate-based melanin inhibiting agents in skin compositions have been reported. However, the main challenge is to provide the desired effect of skin lightening. The topical delivery of active agents into the skin to obtain the desired effect is difficult. Skin is a structurally complex, relatively thick membrane. Hence, penetration of topically applied agents into the affected area of skin may be particularly difficult to achieve. Although many chemical permeation enhancers are known, there is an ongoing need for a skin composition which is highly effective in increasing the rate at which the active agent permeates the skin but does not result in skin damage, irritation, sensitization, or like effects.

Thus, in one aspect the present invention is directed to provide a composition which has enhanced skin permeability, so that the subject who is being treated with the said composition gets the maximum benefit of enhanced efficacy.

The skin composition according to the present invention comprises at least one carbohydrate-based melanin inhibiting agent which according to the present invention may be selected from arbutin, bearberry extract, ascorbyl glucoside, and rutin; incorporated in an ultra low molecular weight aminoglycan polymer gel.

Those skilled in the art know that aminoglycans are polymers formed of disaccharide units. The common aminoglycans include chondroitin sulfate, keratan sulfate, dermatan sulfate and hyaluronic acid or salts of hyaluronic acid. For the purpose of the present invention, aminoglycan selected from chondroitin sulfate, keratan sulfate, dermatan sulfate and hyaluronic acid or its salts; of ultra low molecular weight is used. The preferred aminoglycan used in the skin composition according to the present invention is an ultra low molecular weight hyaluronic acid sodium salt with a molecular weight range of 15,000 to 30,000 Daltons. Such a low molecular weight hyaluronic acid sodium salt is isolated from a natural source of waste egg shells. A process for the isolation and stabilization of hyaluronic acid sodium salt from waste egg shells is subject matter of the inventor's U.S. patent application Ser. No. 11/895,500 published as US Application Publication No. 2008/0051368, now U.S. Pat. No. 7,868,165 (continuation-in-part of U.S. patent application Ser. No. 11/277,489, published as US Application Publication No. 2007/0225484, now abandoned), each of which is incorporated herein in its entirety.

Typically, the skin composition of the present invention comprises the aminoglycan polymer in a concentration from 1% to about 99% by weight and the carbohydrate-based melanin inhibiting agent as described above in a concentration from 1% to 20% by weight, preferably from about 1% to 10% by weight. The weight ratio of the aminoglycan polymer to the carbohydrate-based melanin inhibiting agent typically varies from 99:1 to about 1:2, and preferably from about 10:1 to 1:1 by weight. More preferably, the subject composition contains approximately twice the amount of aminoglycan polymer to the carbohydrate-based melanin inhibiting agent.

The skin composition of the present invention may optionally contain an antioxidant to aid in protection of the skin. Preferred examples of such agents include, without intended limitation, vitamin E, vitamin A, tree tea oil, green tea extract, butylated hydroxyl anisole (BHA), butylated hydroxyl toluene (BHT) and ferulic acid or derivatives thereof. Preferably these agents comprise 0.05% to 15% by weight, more preferably between 0.5% and 5% by weight of the finished skin composition of the present invention.

The skin composition of the present invention may optionally contain one or more conventional and commercially available cosmetically acceptable ingredients suitable for use in such preparations. These ingredients may include materials such as emulsifiers, surfactants, emollients, essential oils, moisturizers, stabilizers, viscosity modifiers, gelling agents, humectants, colorants and the like. Those skilled in the art of cosmetic formulation will recognize that individual compounds will be selected in part based on the method of application being prepared and generally the cosmetic ingredients that may be used to formulate the subject skin composition will be, without intended limitation, ingredients listed in the *International Cosmetic Ingredient Dictionary and Handbook*.

Consequently, the skin composition of this invention is prepared as cosmetically and/or pharmaceutically acceptable forms suitable for such topical application. Such compositions include liquid, lotion, cream, paste, serum, gel and other similar forms. For convenience in packaging, the composition may also be formulated as a dry powder or a tablet to be wetted with water prior to application. The skin composition of the present invention is suitable for topical application to the skin but the method of application may vary depending on the type of composition prepared, for example, the application may be used by spraying, wiping, swabbing, soaking, rubbing and other like methods of application. Thus, the skin composition of the present invention may be prepared in the form of a liquid, lotion, cream, pate, gel, serum, tablet or powder that may be converted into a suitable fluid preparation. The formulation may comprise from about 1.0% to 99% by weight, and preferably between 5% and 20% by weight of the subject skin composition containing a carbohydrate-based melanin inhibitor incorporated in an ultra low molecular weight aminoglycan polymer.

In another aspect of the invention, there is provided a method for lightening hyperpigmented skin, which comprises topically applying to the skin an effective amount of the skin composition for a period of time sufficient to realize a visibly lighter de-pigmented skin.

The skin composition of the present invention is topically applied to the skin in an amount sufficient to visibly lighten the skin.

The hyperpigmented skin or hyperpigmentation that the skin composition of the present invention is used to treat, may include disorders caused by abnormally increased pigmentation, such as melasma or melasma arising during pregnancy ("mask of pregnancy") or as a consequence of oestrone or progestogen contraception; other localized hyperpigmentations by benign melanocytic hyperactivity and proliferation, such as senile pigmental blemishes; disease-related hyperpigmentation; accidental hyperpigmentations such as those due to photosensitization, genetic makeup, chemical ingestion or other exposure, age, and post-lesional scarring.

In a preferred embodiment, the hyperpigmented skin that the skin composition of the present invention is used to treat is the hyperpigmented skin around the eye region.

In a more preferred embodiment of the invention, the hyperpigmentation is the pigmentation (dark circles) around the eye region.

It has been found that the skin composition of the present invention shows unexpectedly higher degree of efficacy and persistence of effect. The efficacy of the treatment involving use of the skin composition according to the present invention was determined on the basis of Melasma Area Severity Index (MASI) score. The MASI system was developed by Kimbrough-Green C K et. al for the assessment of melasma (Kimbrough-Green C K et. al; Arch. Dermatol, 1994; 130:727-733).

The MASI score was measured in a trial involving 16 subjects having hyperpigmented area (dark circles) around the eye region. The improved efficacy was reflected in a quicker visible lightening of the hyperpigmented skin and a more pronounced cumulative effect as evidenced by MASI (Melasma Area Severity Index) scores measured in a trial. FIG. 1 demonstrates the improvements yielded by three weeks of application of the skin composition of the present invention.

Other features of the invention will become apparent in the course of the following descriptions of exemplary embodiments, which are given for illustration of the invention and are not intended to be limiting thereof.

EXAMPLES

Example 1

Preparation of the Skin Composition Formulated as a Cream

| Ingredients | % By Weight |
|---|---|
| Arbutin | 5 |
| Ultra low molecular weight aminoglycan extract | 10 |
| Distilled Water | 60 |
| White beeswax | 3 |
| Paraffin wax | 6 |
| Emulsifier wax | 4 |
| Green Tea Extract | 4 |
| Mixed essential oils (plant) | 7 |
| Methylparaben | 1 |

The above skin composition was formulated into a light white cream by a conventional method. For instance, according to the present invention, the cream was prepared as follows:

The above ingredients namely aminoglycan extract, distilled water, green tea extract, glycerin, methylparaben and arbutin were taken in a 200 ml beaker and heated to a boil while stirring vigorously to obtain an aqueous phase. In a separate 200 ml beaker the white beeswax, paraffin wax and emulsifier wax were added and heated to melt to a uniform consistency. While still a hot melt, the blend of essential oils was added to the melted wax. The aqueous phase was then added into the above blend of wax/oils and stirred gently while allowing to cool to room temperature to obtain a light white cream having uniform consistency.

Example 2

Preparation of the Skin Composition Formulated as a Cream

| Ingredients | Quantity (gms) |
|---|---|
| Cetomacrogol 1000 | 2.0 |
| White soft paraffin | 4.0 |
| Cetostearyl alcohol | 7.0 |
| Light liquid paraffin | 4.0 |
| Essential Oil Mixture | 6.0 |
| Ultra low molecular weight aminoglycan extract | 10.0 |
| Arbutin | 5.00 |
| Disodium hydrogen phosphate | 0.0085 |
| Sodium dihydrogen phosphate | 0.015 |
| Methyl paraben | 0.10 |
| Propyl paraben | 0.02 |
| Propylene glycol | 3.00 |
| Purified water | q.s. 100.0 |

All the oily phase ingredients except essential oil mixture were accurately weighed in a glass beaker to obtain an oily phase. Purified water and propylene glycol mixture were weighed in another glass beaker to obtain an aqueous phase. Aminoglycan extract was homogenized for 5 minutes. The contents in both the beakers were heated till the temperature of oily and aqueous phase was 70° C. At this stage, methyl paraben and propyl paraben were added to the aqueous phase and this mixture was stirred with the help of a glass rod till the paraben dissolves. The aminoglycan extract was added to the aqueous phase and stirred. The aqueous phase was added to oily phase in a stream with continuous stirring. The essential oil mixture was added with stirring at 45° C. and stirring was continued till the cream attains room temperature.

Example 3

Trial Involving Treatment of Subjects with Melasma (Dark Circles) Around the Eye Region Using the Formulation of Example 1

This study involved 16 subjects with mild to severe melasma typified by dark circles around the eyes. The treatment period was three weeks. Based on the data obtained from this study, the composition of the present invention was found to be significantly effective in lightening dark circles around the eyes as evidenced by MASI scoring. Further, the composition of Example 1 lightened the skin of the test subjects in a very short period of time and when use was discontinued, the localized skin lightening did not return for an extended period of time. FIG. 1 demonstrates the improvements yielded by three weeks of application of the formulation of example 1.

Accordingly, it can be seen that skin composition according to the present invention comprising a carbohydrate-based melanin inhibitor incorporated into an ultra low molecular weight aminoglycan polymer exhibits significant lightening of the skin in a very short period and a slower re-pigmentation upon discontinuation of the topical treatment.

What is claimed is:

1. A method for lightening hyperpigmented skin in a subject comprising topically administering to the subject in need thereof an effective amount of a composition consisting of arbutin incorporated into hyaluronic acid sodium salt having molecular weight ranging from 15,000 to 30,000 Daltons, and at least one cosmetically acceptable ingredient selected from the group consisting of white beeswax, paraffin wax, emulsifier wax, green tea extract, methylparaben, cetomacrogol 1000, cetostearyl alcohol, disodium hydrogen phosphate, sodium dihydrogen phosphate, propyl paraben, propylene glycol, liquid paraffin, essential oils and water, wherein the arbutin is present in the composition in an amount of from 1 to 20% by weight and the hyaluronic acid sodium salt is present in the composition in an amount of from 1 to 99% by weight.

2. A method as claimed in claim 1, wherein the hyperpigmented skin is around the eye region.

3. The method according to claim 1, wherein the composition is formulated for topical application.

4. The method according to claim 3, wherein the composition formulated for topical application is in the form of a cream, lotion, paste, ointment, emulsion, gel, foam, liquid spray, a tablet or powder.

5. The method according to claim 1, wherein the weight ratio of arbutin to hyaluronic acid sodium salt varies from 99:1 to 1:2 by weight.

6. The method according to claim 5, wherein said ratio varies from 10:1 to 1:1 by weight.

7. The method according to claim 1, wherein the arbutin is present in the composition in an amount of from 1 to 10% by weight.

* * * * *